US010526575B2

(12) United States Patent
Davies

(10) Patent No.: US 10,526,575 B2
(45) Date of Patent: Jan. 7, 2020

(54) CELL SUSPENSION MEDIUM AND CELL SUSPENSION MEDIUM ADDITIVE FOR THE THREE DIMENSIONAL GROWTH OF CELLS

(71) Applicant: The Provost, Fellows, Foundation Scholars, and the Other Members of Board, of the College of the Holy and Undivided Trinity of Queen Elizabeth, Near Dublin, Dublin (IE)

(72) Inventor: Anthony Davies, Balbriggan (IE)

(73) Assignee: The Provost, Fellows, Foundation Scholars, and the other Members of the Board of the College of the Holy and Undivided Trinity of Queen Elizabeth, Dublin (IE)

( * ) Notice: Subject to any disclaimer, the term of this patent is extended or adjusted under 35 U.S.C. 154(b) by 207 days.

(21) Appl. No.: 14/386,891

(22) PCT Filed: Apr. 2, 2013

(86) PCT No.: PCT/EP2013/056935
§ 371 (c)(1),
(2) Date: Sep. 22, 2014

(87) PCT Pub. No.: WO2013/144372
PCT Pub. Date: Oct. 3, 2013

(65) Prior Publication Data
US 2015/0056701 A1 Feb. 26, 2015

(30) Foreign Application Priority Data

Mar. 30, 2012 (GB) .................... 1205804.6

(51) Int. Cl.
*C12N 5/00* (2006.01)
*A01H 4/00* (2006.01)
(52) U.S. Cl.
CPC .......... *C12N 5/0018* (2013.01); *A01H 4/001* (2013.01); *C12N 5/0025* (2013.01); *C12N 5/0062* (2013.01); *C12N 2500/34* (2013.01); *C12N 2500/50* (2013.01)
(58) Field of Classification Search
None
See application file for complete search history.

(56) References Cited

U.S. PATENT DOCUMENTS

| | | | |
|---|---|---|---|
| 4,956,185 A * | 9/1990 | Cajigas | A23C 9/137 426/43 |
| 2008/0220524 A1 | 9/2008 | Noll et al. | |
| 2008/0220526 A1 | 9/2008 | Ellison et al. | |

FOREIGN PATENT DOCUMENTS

EP          1783209 A1      5/2007

OTHER PUBLICATIONS

Pai, Vandita B., and Saad A. Khan. "Gelation and rheology of xanthan/enzyme-modified guar blends." Carbohydrate polymers 49.2 (2002): 207-216.*
Mao, Ching-Feng, Yuan-Chang Zeng, and Cheng-Ho Chen. "Enzyme-modified guar gum/xanthan gelation: an analysis based on cascade model." Food hydrocolloids 27.1 (2012): 50-59.*
Jones, James A., Jean R. Starkey, and Andris Kleinhofs. "Toxicity and mutagenicity of sodium azide in mammalian cell cultures." Mutation Research/Genetic Toxicology 77.3 (1980): 293-299. (Year: 1980).*
Aguirre-Ezkauriatza, E. J., et al. "Production of probiotic biomass (Lactobacillus casei) in goat milk whey: Comparison of batch, continuous and fed-batch cultures." Bioresource Technology 101.8 (2010): 2837-2844. (Year: 2010).*
Ichi et al., "Effects of Gelling Agents on in Vitro Culture of Plant Tissues', Agricultural and Biological Chemistry," vol. 50, No. 9, 1986, pp. 2397-2399.
International Search Report dated Aug. 26, 2013 for PCT/EP2013/056935.

\* cited by examiner

*Primary Examiner* — Robert J Yamasaki
(74) *Attorney, Agent, or Firm* — Praedcere Law

(57) ABSTRACT

The present invention relates to a cell culture medium additive comprising a xanthan polysaccharide and a mannan polysaccharide, such as a glucomannan or a galactomannan, that supports the growth of cells in suspension, and to a cell culture medium containing the additive. More particularly, but not exclusively, the present invention relates to a cell culture medium additive that supports the formation of multicellular bodies such as spheroids, and prevents sedimentation of cells without adversely affecting the physical properties of the cell culture medium.

19 Claims, 12 Drawing Sheets

CELL SUSPENSION MEDIUM AND CELL SUSPENSION MEDIUM ADDITIVE FOR THE THREE DIMENSIONAL GROWTH OF CELLS

FIELD OF THE INVENTION

The present invention relates to a cell culture medium additive that supports the growth of cells in suspension and to a cell culture medium containing the additive. More particularly, but not exclusively, the present invention relates to a cell culture medium additive that supports the formation of multicellular bodies such as spheroids, and prevents sedimentation of cells without adversely affecting the physical properties of the cell culture medium.

BACKGROUND TO THE INVENTION

Cell based models are extensively used in drug discovery and biomedical research. Cells are typically grown in vitro using two dimensional culture systems or in three dimensions in, for example, expensively engineered bioreactors, solid gels, or hanging drops. Adherent cells attach to the bottom of the cell culture vessels or dishes and remain attached as they grow. In a suspension culture, on the other hand, the cells do not adhere to a fixed substrate, and grow optimally if they float suspended in cell culture medium. Depending on the cell type, these cells may spontaneously form multi-cellular bodies such as spheroids or they may divide rapidly. The advantage of growing cells in suspension is that the cells may either aggregate to form multi cellular bodies or grow and divide freely as single cells. Cells which are grown in conventional suspension culture media passively drift under gravitational force, over very short periods of time, towards the bottom of the culture vessel in which they are maintained. As a consequence these cells are maintained in close proximity to each other at the base of the culture vessel, where at high density, cells experience reduced oxygen and nutrient availability, and elevated levels of metabolic waste products. Consequently, cells growing in this environment may in many cases experience retarded growth rates that can be even further exacerbated by cell-to-cell contact inhibition. This is particularly problematic where it is necessary to grow cells for applications such as the large-scale production of cellular products, for example proteins or glycoproteins.

The passive sedimentation of cells to the bottom of the culture vessel is a widely acknowledged problem with suspension cultures and is dealt with in a number of ways. In small scale culturing facilities, the cell culture medium is changed often to reduce the negative effects of the accumulation of cells at the base of the culture vessel. In larger facilities, where cells are grown in bioreactors, the cells are continually agitated to prevent them from drifting to the bottom of their container. The first solution can be inefficient, labour intensive, expensive, wasteful, and could potentially produce unwanted side effects while the second is expensive and potentially damaging and destructive to the cells and their growth (due to sustained mechanical perturbation of the continuously agitated cells).

When adequately suspended in 3 dimensions, some cell types tend to aggregate into multi-cellular bodies (commonly referred to as spheroids) which in some assay systems resemble tumours found in vivo. These bodies can form either by self-assembly i.e. where cells actively aggregate, by forced aggregation, by cell division, or a combination of all three. Despite the fact that these multi-cellular bodies will not permit rapid growth of cells, if the size and structure of the multi-cellular bodies can be controlled, they represent an extremely valuable research tool due to their physiological relevance in specific research applications. Similarly, pluripotent stem cells may aggregate into multi-cellular bodies known as "embryoid bodies". While these multi-cellular bodies may also be regarded as spheroidal in nature, they are distinct from the tumour-resembling spheroids previously discussed because they may have the propensity to grow to larger sizes. Due to the intrinsic value of pluripotent stem cells, it is thus clear that the cultivation of embryoid bodies is also an important research goal. It is therefore apparent that effective 3-dimensional growth of cells to produce robust model systems is desirable.

Currently, extracellular matrix solid gels such as Matrigel™ and soft agarose are used to grow cells in three dimensions. Matrigel is a naturally derived growth substance which forms a scaffold similar to the extra cellular matrix, and has been used in culture medium to study tumour spheroids and in the development of in vitro metastasis models. The drawback with Matrigel is that this gel must be in a solid state to grow cells in 3-dimensions. Cells grown in such a viscous environment are not easily analysed by automated high throughput imaging systems, as they are difficult to treat with analytical agents such as cellular dyes, and more often than not, the cells do not lie in a single focal plane. Additionally, sampling secreted substances is technically challenging, and Matrigel is not compatible with laboratory liquid handing devices. As such, the experimental workflows using these types of materials are difficult to automate and hence not readily suited to high throughput screening applications.

Alternatively, engineered scaffolds, such as micro-scale solid structures may be used as inserts or built in to culture dishes or culture vessels. Such structures provide a 3-D scaffold made from materials such as functionalised polystyrene that provide a growth matrix for cells to grow into and for tissue like structures, while at the same time permitting adequate perfusion of nutrient to the cells. These scaffolds are extremely expensive to produce and are only compatible with certain cell types. The scaffold also makes it difficult to image cells and it is not readily practical to extract cells grown using this system.

Also, micro-patterned surface technologies have been used to encourage aggregation of cells. However, experiments using such plates have been restricted to specialized micro-plates which are often only provided in a limited range of designs, densities and materials. Round bottom plates of this type are difficult to image, and the surface patterning or micro-features can further interfere with imaging systems (a common complaint is that these technologies can throw off auto focus). Furthermore, cells are forced together in aggregates using these technologies (rather than allowing the aggregates to form passively), and this technology has also proved expensive to use.

Hanging drop technologies present a further solution as they permit the formation of spheroidal cellular aggregates by bringing cells together in close proximity in a controlled way. These technologies are technically cumbersome, requiring a skilled operator to use, and the imaging of cellular samples within this technology can be difficult without using additional or specialized plates.

Passive cell sedimentation is also a problem in a number of other areas of cell based research. For example, in flow cytometry, cells that sediment out of solution can result in an irregularly dispersed cell suspension that can impact results. Flow cytometry probes have difficulty picking up sedimented cells, and if large bodies of sedimented cells are picked up, this can clog the fluidics of the machine. This is a particular problem in high-throughput flow cytometry, where multiple samples are provided in multiwell plates, and manually re-suspending each sample is laborious and technically challenging. In acoustic droplet ejection (ADE) systems, cells sediment to the bottom of a sample and out of the region of the sample that is to be ejected (with current technologies this is a region close to the bottom of the fluid meniscus), resulting in low numbers of dispersed cells. Effective cell suspension is also desirable in electroporation, where it is necessary to maintain cells in effective suspension during the electroporation process. It is similarly desirable to maintain cells in effective suspension for the purposes of lipid-mediated transfection, or lipofection.

OBJECT OF THE INVENTION

It is thus an objective of the invention to provide an additive for a cell culture medium that facilitates the growth of cells in 3-dimensions. It is also an object to allow the cell culture medium to retain liquid-like properties when handled. A further object is to provide an additive for a cell culture medium for the 3-dimensional growth of cells which is easy to manage or dispense such that it may be used in automated laboratories and/or High Throughput Screening systems. A further object is to provide an additive for a cell culture medium which facilitates the creation of cell suspensions for use in applications such as Flow Cytometry, Acoustic Droplet Ejection, lipid mediated transfection and electroporation. A still further object is to provide an additive for a culture medium which facilitates growth of cells in 3-D cell culture which has no toxic effects. A further object is to provide an additive for a cell culture medium which allows the improved diffusion of gases and nutrients required for cell growth compared to solid gel materials such as extracellular matrix gel. A further object is to provide an additive for a cell culture medium which allows cells to be directly observed during cell growth, and monitored by counting. An additional object is to provide an additive for a cell culture medium which allows the cell proliferation progress to be determined by biomass measurement, A further object is to provide an additive for a cell culture medium which allows the monitoring of a diversity of physiological processes at the cellular level. An additional object of the invention is to provide a cell culture medium for any of the above-stated purposes. A further object is to provide a means for precipitating/sedimenting cells out of the suspensions envisaged above.

SUMMARY OF THE INVENTION

According to the present invention there is provided a cell culture medium additive comprising xanthan and a mannan type polymer. Suitable mannan type polymers are galactomannans or glucomannans. The galactomannans may be selected from the group comprising Guar gum, locust bean gum, Tara gum, Fenugreek and Cassia gum. Suitable glucomannans include Konjak. The mannan type polymer may also be an enzyme-modified variant of either a galactomannan or a glucomannan in order to alter the level of interaction between the mannan type polymer and the xanthan. The mannan type polymer may comprise a blend of one or more different specific forms of mannan.

The xanthan and mannan-type polymer are present in amounts of between 60:40 and 20:80 w/w. Suitable ratios include 55:45; 50:50; 45:55; 40:60; 35:65: 30:70 and 25:75. Preferably, the polysaccharides are present in amounts of between 60:40 and 30:70 w/w. In one embodiment, the polysaccharides are present in an amount of 50:50 w/w.

In embodiments of the invention wherein the mannan-type polymer comprises a galactomannan, the galactomannan preferably comprises a galactose content of at least 16% by weight and at most 33% by weight. Suitable galactose contents include 18%; 20%; 22%; 24%; 26%; 28%; 30% and 32% by weight. In one embodiment, the galactomannan comprises a galactose content of approximately 20% by weight. The galactose content of the galactomannan may be adjusted by way of enzyme modification. The enzyme used may be an α-galactosidase.

According to the invention, there is also provided a cell culture medium containing an additive comprising xanthan and a mannan-type polymer. The cell culture medium may be suitable for use as a cell culture growth medium for growing cells, and/or suitable for use as a cell suspension medium for keeping cells in suspension for specific other purposes such as Acoustic Droplet Ejection, flow cytometry, lipid mediated transfection or electroporation. The cell culture medium may comprise any conventional medium suitable for growing or suspending cells. For example, such media may be selected from—but not limited to—the group comprising: Dulbecco's modified Eagle's medium (DMEM); medium 199, Roswell Park Memorial Institute medium (RPMI), Ringer's solution, Eagle's minimal essential medium (EMEM), Phosphate buffered saline, or variants thereof. In an embodiment of the invention the additive is present in the cell culture medium in an amount of between 0.012% and 0.36% w/v inclusive. Suitably, for suspending single cells and for the formation of spheroids, the additive may be present in the cell culture medium for example at 0.04%, 0.05%, 0.06%, 0.07%, 0.08%, 0.09%, 0.1%, or 0.11% w/v. In one embodiment, the additive is present in the cell culture medium in an amount of about 0.06% w/v. Suitably, for the formation of large multi-cellular bodies such as embryoid bodies, the additive may be present in the cell culture medium at between 0.18% and 0.3% w/v inclusive, for example at 0.2%, 0.22%, 0.24%, 0.26%, 0.28%, or 0.3% w/v. For this purpose, the additive is preferably present in the cell culture medium in an amount of about 0.24% w/v. Suitably, for dispensing suspended cells by way of acoustic droplet ejection, the additive may be present in the cell culture medium at between 0.012% and 0.06% w/v inclusive, for example at 0.018%, 0.024%, 0.03%, 0.036%, 0.042%, 0.048 or 0.054% w/v. In acoustic dispensing embodiments for certain cell types, the additive is preferably present in the cell culture medium in an amount of about 0.018% w/v.

The invention also provides a method of culturing cells in 3-dimensions comprising growing cells in the presence of a culture medium to which xanthan and the mannan type polymer have been added. Animal, plant and microbial cells may all be cultured in this way.

The presence of the additive in the cell culture medium prevents cells from drifting towards the base of the culture vessel, but still permits the aggregation of cells into three-dimensional structures. The additive has proved to be non-toxic to the cells at even the highest concentrations tested. As the culture medium containing the additive is liquid rather than a gel type material, it is easy to manage or dispense the culture medium and can be automated in the laboratory for high throughput screening, liquid handling and other such techniques. Additionally, the viscosity of the cell culture medium does not change notably when the additive is added, nor does the additive affect the optical transparency of the cell culture medium, or dramatically affect the rapid diffusion of gases and nutrients, which is frequently a problem with gel type media. In particular culture medium containing the additive of the invention has been successfully used in flow cytometry and acoustic droplet ejection. In addition, culture medium containing the additive of the invention may be used in electroporation and lipid-mediated transfection.

Cells growing in media containing the additive of the invention can remain in suspension for a substantially prolonged period of time. Such cells show improved viability and cell growth, when compared to equivalent cells grown in a control medium without the presence of the additive. It has been shown that cells grown in cell culture media containing the additive of the invention may express or secrete products at notably higher concentrations than cells grown in traditional culture media. This could be useful where cells are used to produce antigens or other cell products on a large scale basis, as yields from a given cell population could be dramatically increased if grown in cell culture media containing the additive.

Furthermore, it has been shown that cells such as those derived from prostate and breast cancer, can spontaneously form multi-cellular tumour-like structures (commonly referred to as spheroids) when grown in a cell culture medium containing the additive. It has been shown that cells in such spheroids demonstrate different gene expression patterns similar to such tumour cells in vivo, and as distinct from the gene expression patterns of corresponding tumour cells grown in vitro in 2D. This makes the invention particularly useful for tumour modelling studies in cancer research.

The capacity of the culture medium containing the additive to hold cells in suspension is not disrupted over the normal physiological range of pHs and temperatures, with the proviso that the concentration of the polysaccharides in the medium remains in the range necessary to achieve suspension.

When it is no longer desired for the cells to remain in discrete suspension, and they may be required to settle/sediment at the base of the culture vessel, it is a simple matter to dilute out the additive by the addition of fresh medium, past the concentration at which the cells would normally be suspended. Cells then behave as they do in a typical culture medium, and sink/sediment to the bottom of the culture vessel. Thus the medium of the invention is particularly advantageous, since it can be modified to grow the cells in suspension and then to allow them to settle.

While it is a simple matter to allow cells to precipitate/sediment out of suspension by diluting the additive to an ineffective amount, on occasions, this may not be wholly practical. For example, where microwell plates are being used, each well may lack the necessary volume to allow for an effective amount of dilution. Accordingly, an alternative manner of precipitating/sedimenting cells is also desirable. The invention further provides for a means by which this may be achieved through the application of a polysaccharide-digesting enzyme that breaks down the additive, thereby reducing the capacity of the medium to suspend cells, and hence allowing the cells to precipitate/sediment out of suspension.

A further advantage is that the polysaccharides used in the additive of the invention have been afforded GRAS status (Generally Recognised as Safe) by the FDA, so any products produced in the medium are safe for human use. Furthermore, the polysaccharides are not derived from animal products. As such they are free from the contamination concerns associated with animal products, such concerns including, for example, prion contamination.

When added to a cellular culture medium, the additive-medium solution may settle slightly, leaving an additive-free supernatant. This is advantageous because the supernatant may be replaced, thereby permitting periodic partial replenishment of nutrient media without perturbing the suspended cells.

Since cell culture medium containing the polysaccharides have been used to grow tumour spheroids, it is possible to use the medium to facilitate formation of stem cell colonies.

A further advantage is that the cell culture medium additive enables more efficient dispensing of cells by acoustic droplet ejection (ADE), because it achieves a more uniform dispersion of cells in a cell suspension that is to be used as a source sample in ADE. ADE technologies are now widely used in cell based screening, and at present they are primarily used in assay preparation (most often compound dispensing). One application that has received a great deal of interest is using ADE technology for cell dispensing. However, one major drawback of using ADE for these types of application is the fact that cells must be near the surface of the liquid (the point where the acoustic energy is focused). In normal media cells rapidly fall out of suspension and consequently are dispensed in now concentrations, or do not get dispensed at all. By contrast, using cell culture media containing the additive of the invention ensures that cells remain in suspension for longer and as a consequence, reside in the zone of the well where the acoustic energy is focused, hence resulting in vastly improved cell transfer from source plate to destination plate.

An additional advantage is that the cell culture medium additive facilitates serial dispensing cells in suspension from single tips of conventional positive displacement cell dispensing robots such as the Matrix Hydra, provided by Thermo Fisher Scientific, because it will permit a more constant number of cells dispensed from well to well, whereas with media without the additive, the majority of cells will be lost in the first dispense. Furthermore, the additive is also of use in micro fluidic devices because it allows the flow rate of the fluidic devices to be reduced while still keeping cells suspended and moving through the device.

BRIEF DESCRIPTION OF THE DRAWINGS

FIGS. 10a and 10b show spheroids grown in cell culture medium wherein FIG. 10a shows A549 cells grown for 5 days in RPMI medium containing the cell culture medium additive and FIG. 10b shows CHO-K1 cells grown for 5 days in RPMI medium containing the cell culture medium additive, wherein both images were produced using a High Content Analysis imaging system.

DETAILED DESCRIPTION OF THE INVENTION

Figure 1B:
FIGS. 1a and 1b show a comparison of cells grown in Dulbecco's Modified Eagle Medium (DMEM) with and without the cell culture medium additive respectively.
Figure 1A:
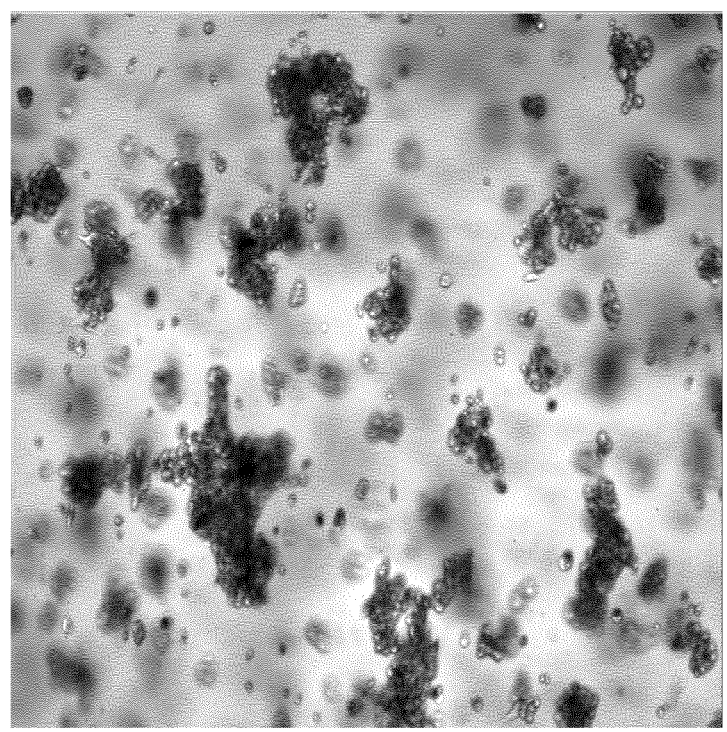

It has been found that applying a cell culture medium additive comprising a blend of a xanthan polysaccharide and a mannan polysaccharide to a cell culture medium has the surprising effect of retaining deposited cells in suspension, and preventing the cells from falling out of suspension (or sedimenting). It has been observed that a cell culture medium containing the additive can suspend cells in a notably more effective way than the same cell culture medium on its own. This additive is effective in the cell culture medium at very low concentrations, thereby minimally affecting the viscosity of the cell culture medium when it is being handled/dispensed.

Cell culture medium containing the additive has demonstrated low viscosity under medium to high shear stress, but high viscosity under low shear stress. Typical handling and/or pouring operations give rise to medium to high shear stresses, and under these conditions, the cell culture medium containing the additive display a low viscosity, similar to the behaviour of the same cell culture medium without the additive (see Example 6 below). By contrast, suspended cells falling out of suspension exert low shear stresses. In this environment, cell culture medium containing the additive exhibits a viscosity sufficiently high to prevent the cells from falling out of suspension. The high viscosity under low shear stress and low viscosity under medium to high shear stress characteristics exhibited by the additive when in solution have been attributed to an interaction between the xanthan polysaccharide and the mannan polysaccharide. The exact xanthan and mannan polysaccharides used affects the extent of this interaction, and thus the extent to which the additive demonstrates these described characteristics.

In addition, cell culture medium containing the additive has proved effective in the formation of spheroids. While spheroids may form through cell aggregation or cell division, it is known that formation of spheroids by cell division takes a notably longer time. Cells grown in cell culture media containing the additive have been observed to form spheroids comparatively quickly (within 24 hrs), and as such, it is believed that the spheroids formed in cell culture media containing the additive form by way of cell aggregation. Thus, while cell culture medium containing the additive can prevent cells from falling out of suspension, these media do not appear to inhibit cell aggregation and formation of multi-cellular bodies such as spheroids.

Typically, the mannan polysaccharide is either a galactomannan or a glucomannan. While the characteristics of the additive will now be discussed with respect to a xanthan polysaccharide—galactomannan polysaccharide blend, but it will be appreciated that similar teachings apply to the use of xanthan polysaccharide—glucomannan polysaccharide blends Xanthan gum is a polysaccharide that comprises extracts of the bacterium *Xanthomonas campestris*. The optimum interaction obtained between a galactomannan and xanthan in the additive of the invention depends on the ratio of the two polysaccharides and the proportion of galactose (by weight) in the galactomannan. Galactomannans have an unbranched chain of mannose units as their backbone with galactose side chains distributed along the backbone. The distribution of galactose along the backbone has been extensively researched and is well understood (Reid, Edwards, Gidley, & Clark, 1992). Native forms of different galactomannans exhibit different mannose:galactose proportions. For example, native Fenugreek gum exhibits mannose:galactose proportions of ~50:50 (i.e. 50% galactose by weight); native Guar gum (extracts of the seeds of *Cyamopsis tetragonoloba*) exhibits proportions of ~66:33 (i.e. 33% galactose by weight); native Tara gum (extracts of the seeds of *Caesalpinia spinosa*) exhibits proportions of ~75:25 (i.e. 25% galactose by weight); and native locust bean gum (extracts of the seeds of *Ceratonia siliqua*) exhibits proportions of ~80:20 (i.e. 20% galactose by weight). Guar gum, locust bean gum (LBG), Tara gum, Fenugreek and Cassia (extracts from the seeds of *Senna obtusifolia*) are the galactomannans available in large commercial quantities. There are many other similar products available in nature but few are commercially available.

Without wishing to be bound to a particular theory, it is believed that the more galactose removed from the backbone of a galactomannan, the more regions of free mannan chain are available for interaction with xanthan. For the mannan to be able to interact with xanthan it must have regions of free mannan chain accessible to the xanthan molecules. However, a pure mannan chain is, in its native form, insoluble, as is exemplified in materials such as ivory nut mannan. Testing has suggested that the minimum galactose content required to achieve galactomannan solubility, and thus, interaction with xanthan, is a blend with mannose:galactose proportions of ~84:16 (i.e. 16% galactose by weight). Therefore, for a mannan to interact with xanthan, it must also contain structures that interfere with internal mannan/mannan crystallisation and render the mannan polysaccharide soluble in water. In the galactomannans mentioned above, this role is performed by the galactose sidechains.

Glucomannans are quite similar and require the same distinguishing features as the galactomannans—i.e. regions of free mannan chain must be available to interact with the xanthan, but the glucomannan must still be soluble. In this case, co-polymer regions of glucose result in solubility. Examples of suitable glucomannans include Konjak (extracts from the stem of the plant *Amorphophallus konjac*).

As described above, the galactose content of the galactomannan affects the extent to which the galactomannan can interact with xanthan. Too much galactose reduces the amount of free mannan chain available to interact with the xanthan, but too little galactose renders the galactomannan insoluble. Accordingly, the maximum possible interaction between a galactomannan and xanthan is dependent on the galactose content of the galactomannan. In addition, the galactose content of the galactomannan also affects the he optimum xanthan:galactomannan blend ratio for achieving the maximum interaction between the two polysaccharides. Where a galactomannan has a high galactose content, comparatively low levels of free mannan chain are available for interaction with xanthan. As a result, a blend ratio containing comparatively high levels of the galactomannan must be provided to achieve the maximum interaction for this blend. For example, native Guar gum (~33% galactose by weight) has an optimum interaction with xanthan at a xanthan:Guar blend ratio of around 20:80 w/w (i.e. 80% Guar by weight). However, even at this blend ratio (which constitutes the maximum interaction for this particular combination of polysaccharides), the interaction is comparatively weak, and if used as an additive in accordance with the invention, the additive concentration required in a cell culture medium to give adequate cell suspension is comparatively high. This comparatively high concentration, notably increases the viscosity of the medium, regardless as to whether or not it is subjected to shear force, which can lead to handling and imaging difficulties—particularly in automated laboratories, and/or High Throughput Screening systems.

Galactomannans may be modified to alter their galactose content. As is well understood in the art, enzymes can be used to remove a very specific portion of the galactose side chains. The exact amount of galactose removed can be controlled by the level of enzyme used, length of time of the reaction and other parameters typically used to control an enzyme reaction such as pH and temperature. α-galactosidases are typically used for this purpose. α-galactosidases may be refined from natural sources, but are commonly produced in nature in conjunction with β-mannosidases, and must be isolated from β-mannosidases before use (β-mannosidase would cleave the mannose backbone of the galactosidase).

Figure 2B:
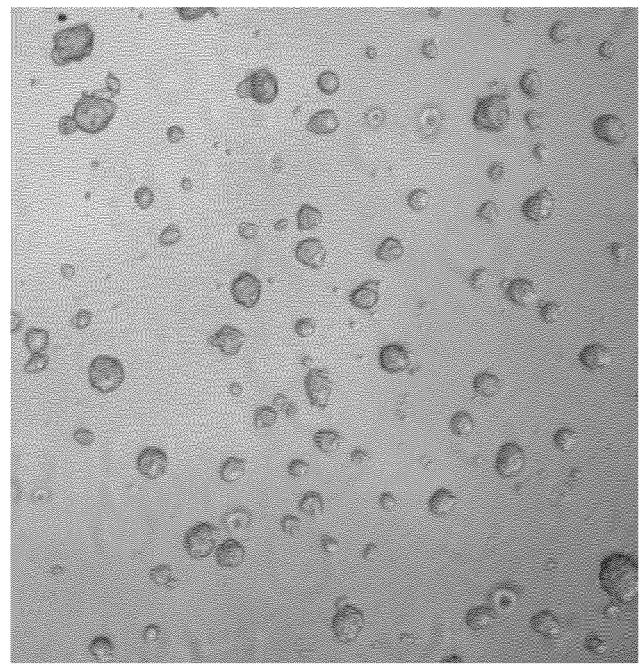
FIGS. 2a and 2b show spheroids grown in cell culture medium containing the additive imaged using a High Content Analysis imaging system.
Figure 2A:
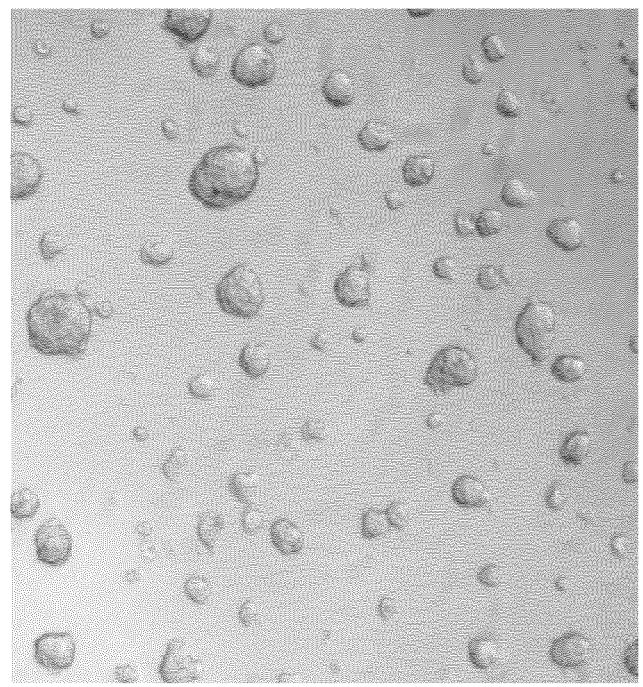

A Guar gum which has had galactose removed to give a mannose:galactose proportion of ~80:20 (i.e. 20% galactose by weight) has an optimum interaction at a xanthan:modified Guar blend ratio of around 50:50 w/w and exhibits a much stronger interaction than the optimum interaction of a xanthan:native Guar blend. As a result of this increased interaction, this xanthan:modified Guar blend, if used as an additive, can be used in a carrier (such as a cell culture medium) at comparatively low concentrations compared to a xanthan:native Guar blend while still displaying the desired cell suspension characteristics. This comparatively low concentration does not notably affect the viscosity of the medium for either handling or imaging activities. This blend exhibits a broad synergetic peak, and a blend ratio of anywhere between 60:40 and 30:70 w/w could be used to achieve the desired cell suspension, albeit at a slightly higher concentration when added to a carrier.

Tests carried out using this xanthan:modified Guar blend (50:50 w/w; guar enzymatically modified by α-galactosidase to give a mannose:galactose ratio of approx. 80:20 w/w) have shown that it is effective as an additive in a carrier (e.g. a cell culture medium) at a concentration of between 0.012% to 0.36% w/v. Below this threshold, the cell culture medium containing this additive begins to lose its cell suspension characteristics, and above this threshold, the viscosity of the cell culture medium begins to increase comparatively and/or solubility problems occur. For suspension of individual cells, and for the formation of multicellular bodies such as spheroids, best results were obtained using this blend as an additive in a carrier at a concentration of between 0.04% and 0.08% w/v inclusive, and preferably at about 0.06% w/v. For the formation of larger multicellular bodies such as embryoid bodies, it was found that a greater concentration of the additive was required. It was found that for this purpose a concentration of between 0.18% and 0.3% was suitable, preferably between 0.22% and 0.28%, and most preferably at about 0.24%. Lower concentrations were found to be most effective for Acoustic Droplet Ejection purposes, with a suitable concentration range being between 0.012% and 0.06% w/v inclusive, with a most preferable concentration for many cell types being at about 0.018% w/v.

It has been observed that adding the additive to a cellular culture medium may result in the slightly settling of the additive-medium solution, leaving an additive-free supernatant (approx 5-20% of total volume of medium). This may be replaced, thereby permitting periodic partial replenishment of nutrient media It will be understood that different xanthan:mannan blends will exhibit varying levels of interaction depending on the blend ratio used, and the extent to which the mannan comprises free mannan chain capable of interacting with the xanthan. As the level of interaction is altered, the optimum concentration at which the blend should be used as an additive in a carrier may also alter.

Example 1—Spheroid Formation in Cell Culture Media Containing the Additive

Freshly trypsinised SKBR3 breast cancer cells were seeded at a density of $0.9 \times 10^4$ cells/100 μl in DMEM either in the presence (FIG. 1*a*) or the absence (FIG. 1*b*) of 0.06% w/v cell culture medium additive [blend of xanthan and enzyme-modified guar (50:50 w/w; guar enzymatically modified by α-galactosidase to give a mannose:galactose ratio of approx. 80:20 w/w)]. Cells were seeded in Nunc F96 Microwell plates and were incubated for 120 hours at 37° C./5% $CO_2$ and 95% humidity. Cells were then imaged at 4× magnification using an IN Cell Analyser High Content Analysis imaging system. As can be seen, the cells grown in the presence of the cell culture medium additive (FIG. 1*a*) show notable spheroid formation, whereas the cells grown in the absence of the cell culture medium additive show little spheroid formation.

Example 2—Imaging of Spheroids in Cell Culture Media Containing the Additive

Freshly trypsinised Prostate cancer cells were seeded at a density of $0.9 \times 10^4$ cells/100 μl in DMEM containing 0.06% w/v cell culture medium additive [blend of xanthan and enzyme-modified guar (50:50 w/w; guar enzymatically modified by α-galactosidase to give a mannose:galactose ratio of approx. 80:20 w/w)] in a 'Hydrocell' low binding 96-well plate (Nunc) and incubated for 72 hours at 37° C./5% $CO_2$ and 95% humidity. Cells were then imaged at 4× magnification using an IN Cell Analyser 1000 High Content Analysis imaging system. Both FIGS. 2a and 2b illustrate the results of this imaging. The images produced clearly illustrate that it is possible to conduct High Content Analysis on cells grown in the cell culture containing the cell culture medium additive.

Figure 10A:
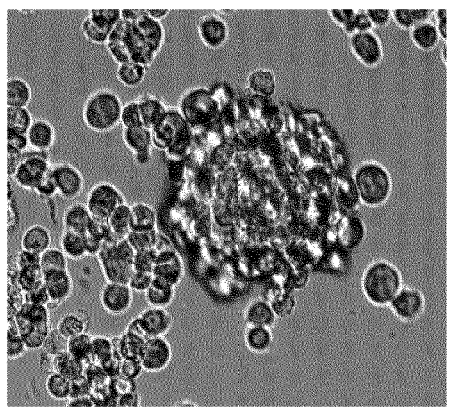
Figure 10B:
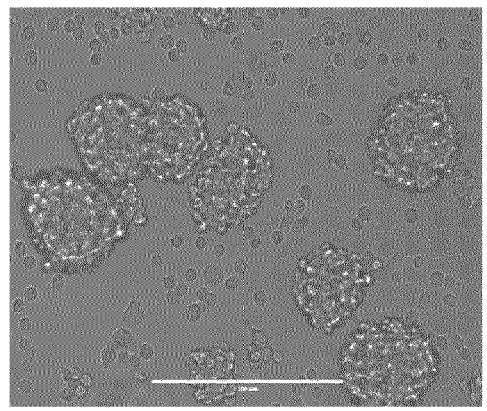

Subsequent experiments performed under similar conditions for five days (cells grown in RPMI containing 0.06% w/v cell culture medium additive [blend of xanthan and enzyme-modified guar (50:50 w/w; guar enzymatically modified by α-galactosidase to give a mannose:galactose ratio of approx. 80:20 w/w)]) resulted in spheroid formation for A549 cells (FIG. 10a) and CHO-K1 cells (FIG. 10b).

Figure 3:
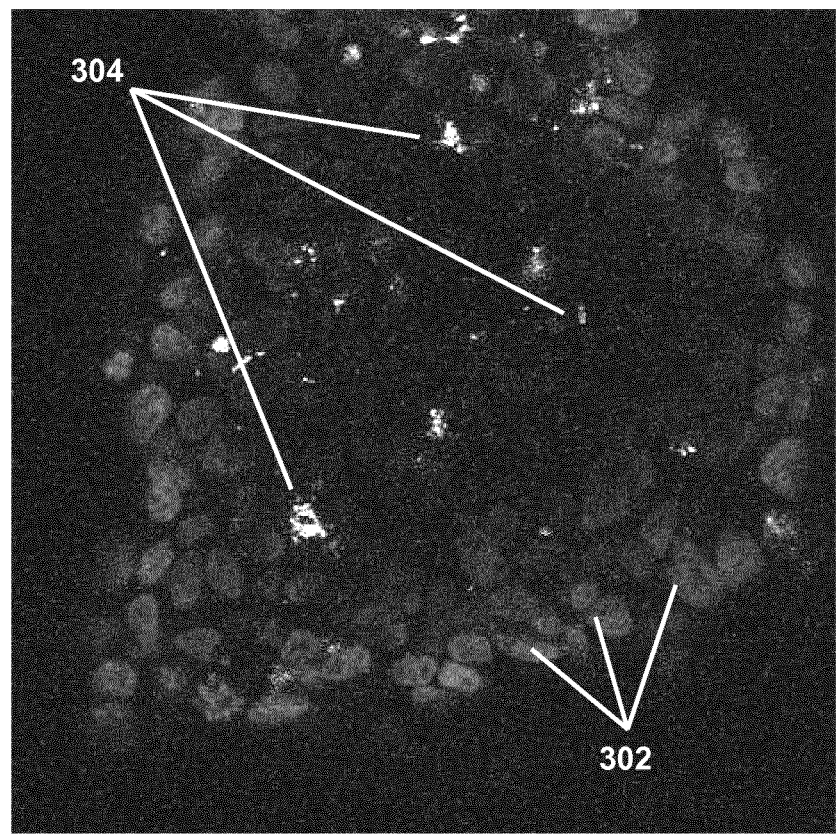
FIG. 3 is a confocal microscopy image of a prostate tumour spheroid seeded in cell culture medium containing the additive showing a viable outer mantle of cells surrounding a region of dead and/or necrotic cells.

Example 3—Characterisation of Spheroids in Cell Culture Media Containing the Additive Freshly trypsinised Prostate cancer cells were seeded in DMEM containing 0.06% w/v cell culture medium additive [blend of xanthan and enzyme-modified guar (50:50 w/w; guar enzymatically modified by α-galactosidase to give a mannose:galactose ratio of approx. 80:20 w/w)] at a density of 1×105 cells/500 in a Lab-Tek chamber slide (Thermo Scientific) and incubated for 48 hours at 37° C./5% $CO_2$ and 95% humidity. Spheroids produced were then subsequently stained with Hoechst (blue fluorescent DNA dye) and propidium iodide, and imaged at 40× magnification using a Zeiss Meta Confocal microscope (FIG. 3). The imaged spheroid comprises a viable outer mantle of cells 302 stained in blue (Hoechst) surrounding a region of dead and/or necrotic cells 304 stained in red (propidium iodide). Spheroids of this type are considered to be more tumour-like than cells grown in 2D.

Example 4—Increased Cellular Expression/Excretion of Antigens in Cells of Spheroids Freshly trypsinised Prostate cancer cells were seeded at a density of $0.9 \times 10^4$ cells/100 µl in either:
  DMEM in Nunc F96 Microwell plates (2D environment);
  DMEM in Nunc F96 Microwell plates, and covered with a layer of containing 0.06% w/v cell culture medium additive [blend of xanthan and enzyme-modified guar (50:50 w/w; guar enzymatically modified by α-galactosidase to give a mannose:galactose ratio of approx. 80:20 w/w)] (2D environment); or
  DMEM containing 0.06% w/v cell culture medium additive [blend of xanthan and enzyme-modified guar (50:50 w/w; guar enzymatically modified by α-galactosidase to give a mannose:galactose ratio of approx. 80:20 w/w)] in Nunc 'Hydrocell' low binding 96-well plates (3D environment).

Figure 4:
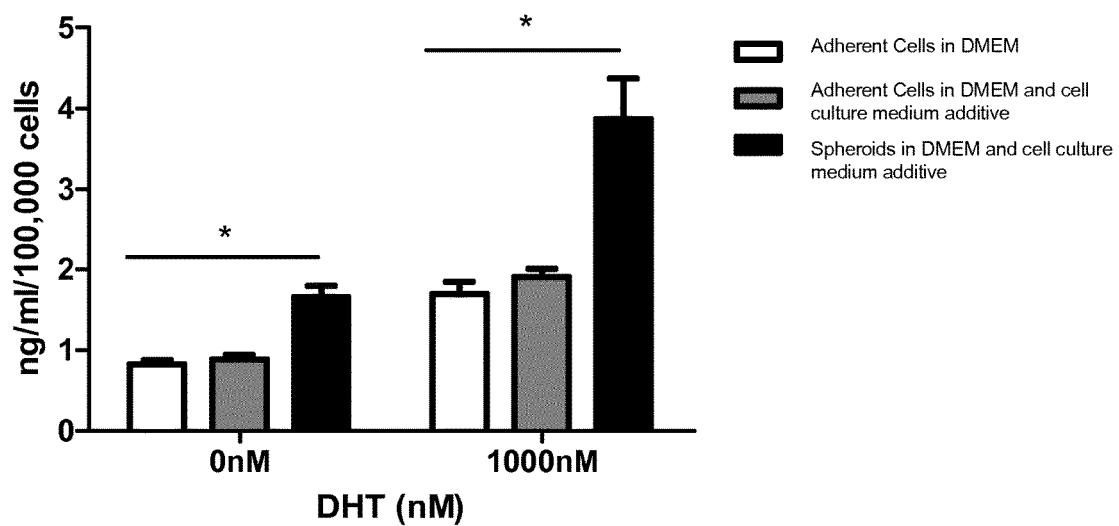
FIG. 4 shows a comparison of expression levels of prostate tumour marker PSA (Prostate Specific Antigen) in adherent cells grown in DMEM cell culture medium, adherent cells grown in DMEM containing the additive, and spheroid cells grown in DMEM containing the additive.

The cells were incubated in the presence or absence of Dihydrotestosterone (DHT) (1000 nM) for 120 hours at 37° C./5% $CO_2$ and 95% humidity. Cell lysates were collected and prepared for evaluation of PSA levels, and viable cell number was assessed for each plate using AlamarBlue in order to ensure that Prostate Specific Antigen (PSA) levels could be corrected to viable cell count. PSA levels were evaluated with a commercially available kit (Quantikine Human Kallikrein 3/PSA Immunoassay, R&D systems). The assay was performed following manufacturer's guidelines. Values represent the mean of three replicates±standard error of the mean. *, p<0.05. The results are shown in FIG. 4. As can be seen, cells of the spheroids grown in the presence of DHT display dramatically increased levels of PSA, illustrating that prostate cells grown in 3D produce significantly greater quantities of the prostate tumour marker PSA than cells grown in 2D. The production of this protein is believed to be directly associated with the hypoxic conditions that are a characteristic of solid tumours such as those associated with prostate cancer. It can be inferred from these results that cells grown in cell culture media containing the additive of the invention may express or excrete products of interest at notably higher concentrations than cells grown in traditional culture media. This could be useful where cells are used to produce antigens or other cell products on a large scale basis, as yields from a given cell population could be dramatically increased if grown in cell culture media containing the additive.

Figure 5:
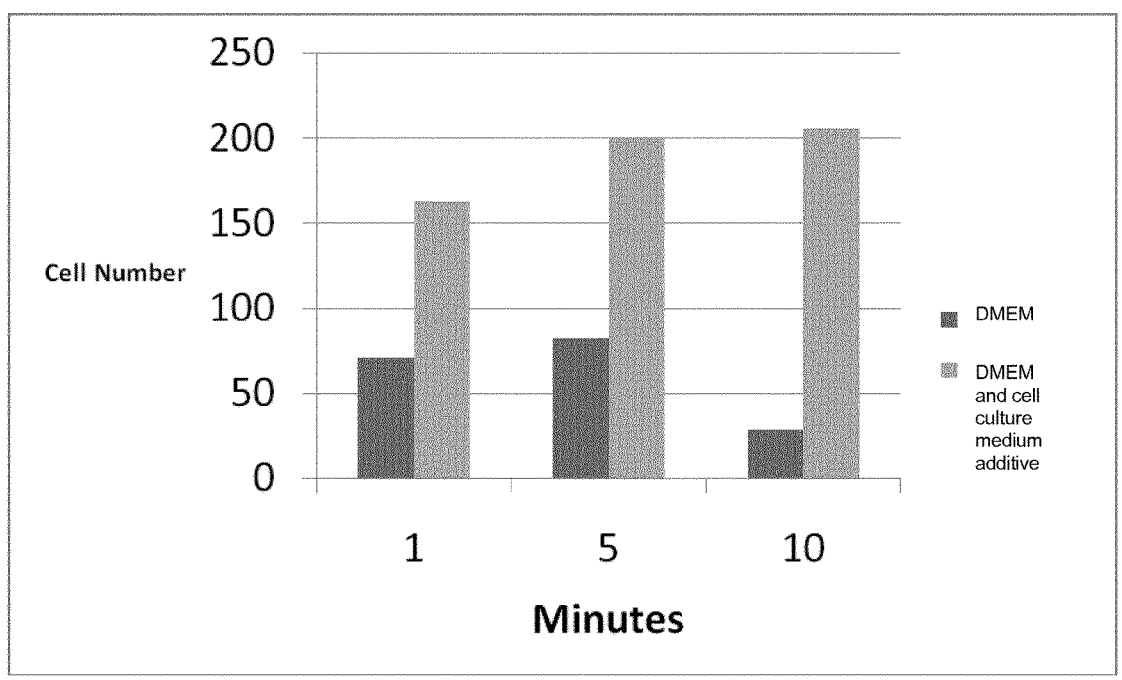
FIG. 5 shows a comparison of the cell numbers dispensed from cell suspensions with and without the cell culture medium additive onto a destination plate using ADE (Acoustic Droplet Ejection) technology.

Example 5—Improved Acoustic Droplet Ejection Using Cell Culture Media Containing the Additive Suspensions comprising A549 cells (density of $5 \times 10^4$/ml) in DMEM, standard Penicillin/Streptomycin 5000 IU/5000 µg/ml and 10% v/v foetal bovine serum (FBS) either with or without 0.06% w/v cell culture medium additive [blend of xanthan and enzyme-modified guar (50:50 w/w; guar enzymatically modified by α-galactosidase to give a mannose:galactose ratio of approx. 80:20 w/w)] were transferred into 384 well source plates in 50 µl measures. After thorough mixing of the cells, the source plates were transferred into an ECHO 550 acoustic dispensing system. 100 nl samples of cell suspension were dispensed over 5 minute periods into a 384 destination plate for periods ranging from 1 to 5 minutes. Cells were then allowed to attach to the bottom of the destination plate and then fixed and stained with the DNA dye Hoechst. The results are shown in FIG. 5. These results show that the number of cells transferred is dramatically increased when suspended in DMEM containing the cell culture medium additive of the invention. This illustrates the efficacy of using the cell culture medium additive of the invention in Acoustic Droplet Ejection technologies.

Through further studies of acoustic droplet ejection, it was determined that for many cell types, applying the cell culture additive at a lower concentration gave even more effective results. In particular, it was apparent that a preferable concentration range for dispensing cells by way of Acoustic Droplet Ejection was between 0.012% and 0.06% w/v of the additive (in the formulation mentioned above), with particularly effective results for a considerable number of cell types being achieved at a concentration of about 0.018% w/v.

Example 6—Liquid Handling Characteristics of Cell Culture Media Containing the Additive DMEM containing 0.06% w/v cell culture medium additive [blend of xanthan and enzyme-modified guar (50:50 w/w; guar enzymatically modified by α-galactosidase to give a mannose:galactose ratio of approx. 80:20 w/w)] has been tested on a variety of laboratory liquid handling devices such as automated and manual air and positive displacement systems, and peristaltic and syringe solenoid dispensers. In all cases, the performance of the cell culture medium handled was determined by weighing the volumes dispensed. The performance of the cell culture medium containing the additive was compared with the performance of the normal medium equivalent (not containing the additive). In all cases (with the exception of acoustic droplet ejection technologies), no significant difference was observed between medium containing the additive and the same medium without the additive. In the case of acoustic droplet ejection technologies, in order to achieve an equivalent dispensed volume of cell culture medium containing the additive and dispensed volume of normal cell culture medium, it was necessary to dope the cell culture medium containing the additive with a doping agent comprising 10% foetal calf serum, 10% foetal bovine serum or an equivalent percentage of seroalbumen. Cell culture medium containing the additive exhibited a smaller droplet volume upon dispensing, and addition of the doping agent counteracted this reduction, achieving a similar droplet volume to that of normal cell culture medium. These results all illustrate that the cell culture medium containing the additive has a substantially similar viscosity to the same medium without the additive when it is being handled. Therefore it is well suited for use with automated liquid dispensing technologies as are common in High Throughput Screening laboratories.

Figure 16:
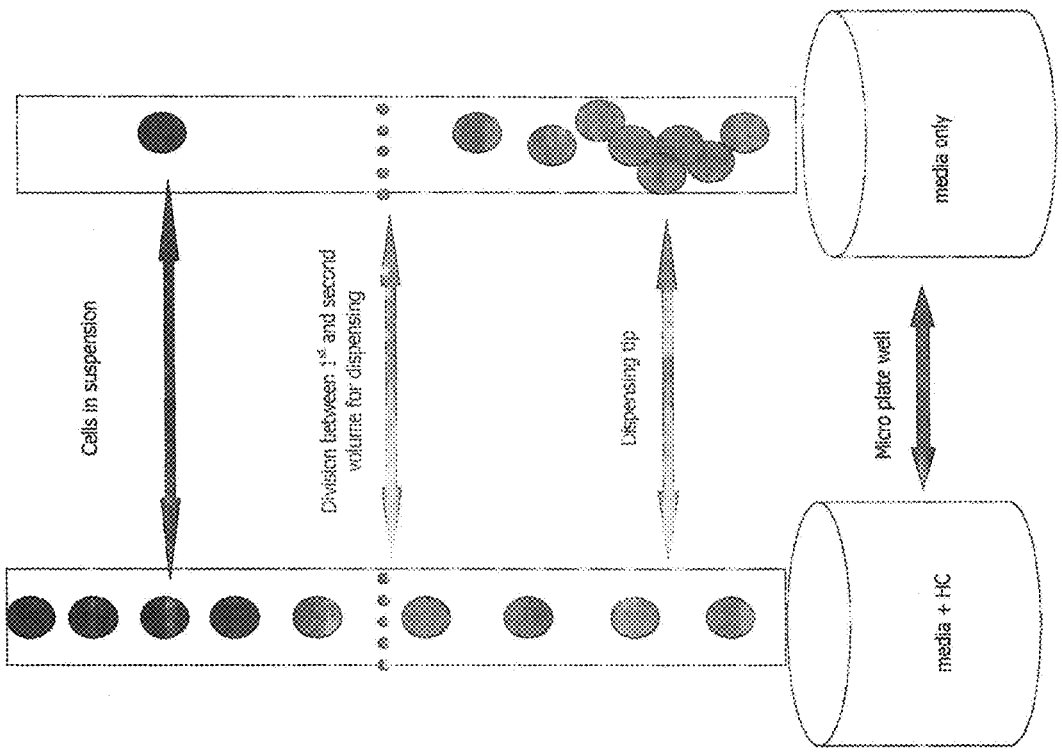
FIG. 16 is a schematic illustrating the benefits of using media containing the cell culture medium additive (designated "HC" in the figure) as a liquid handling aid.

Cell culture media containing the additive is also useful for serial dispensing cells in suspension from a single tip because it will permit a more constant number of cells dispensed from well to well, whereas with media without the additive, the majority of cells will be lost in first dispense. This is illustrated in the schematic of FIG. 16, wherein the dispensing tip on the left comprises cells suspended in cell culture media containing the additive (designated "HC" in the figure), whereas the dispensing tip on the right comprises cells suspended in cell culture media without the additive. This is particularly relevant to tip based liquid handling robots, because such robots will dispense many times from one tip before re-filling is required. Sedimentation of cells may lead to large differences between cell number (i.e. large number at the beginning of the dispensing cycle and few towards the end).

In general, the use of culture media containing the additive in micro fluidic devices means that the flow rate of the fluidic devices can reduced while still keeping cells suspended and moving through the device.

Example 7—Toxicity of Cell Culture Media Containing the Additive

The toxicity of the cell culture medium containing the additive was tested by staining Prostate cancer cells grown in DMEM containing 0.06% w/v cell culture medium additive [blend of xanthan and enzyme-modified guar (50:50 w/w; guar enzymatically modified by α-galactosidase to give a mannose:galactose ratio of approx. 80:20 w/w)] with DRAQ7 (far-red fluorescent DNA dye produced by Biostatus Ltd) and propidium iodide. No increase in cell death was observed when compared with cells grown in corresponding normal medium that did not contain the additive. In fact, large increases in cell proliferation were observed when cells such as HUT78 T-lymphocyte cell lines were tested.

Example 8—Gas and Nutrient Diffusion Characteristics of Cell Culture Media Containing the Additive An assessment of the rapid diffusion of gases and nutrients in cell culture medium containing the additive was performed, and the following observations were made:

(i) High molecular weight molecules such as DNA intercalating dyes such as Hoechst and propidium iodide, readily diffuse through cell culture medium containing the additive (see Example 3);
(ii) PSA levels in cells grown in 2D in cell culture medium containing the additive are no different from those grown in normal medium (see Example 4). It has been well documented that PSA production is elevated when cells were placed under hypoxic conditions.

Example 9—Alternative Formulations

Other suitable formulations of the additive include: xanthan and cassia gum; xanthan and locust bean gum; xanthan and tara gum; xanthan and fenugreek gum; and xanthan and *konjac*. These formulations comprise native or enzyme-modified forms of the mannan-type polymer in order to ensure that sufficient free mannan chain is available to interact with the xanthan to achieve a high viscosity at low shear stresses and low viscosity at medium-high shear stresses when the additive is in solution, without rendering the mannan-type polymer insoluble. In the case of the galactomannans, the total galactose content is between 33% and 16% by weight. Alternatively, a plurality of mannan-type polymers is used in combination in a mannan formulation to achieve the desired quantity of free mannan chain required for an acceptable level of interaction with the xanthan. Single mannans or mannan formulations may exist in any of the following xanthan:mannan ratios: 60:40; 55:45; 50:50; 45:55; 40:60; 35:65: 30:70; 25:75 or 20:80 by weight. When applied to a cell culture medium, the additive is applied at any of the following concentrations: 0.03%, 0.04%, 0.05%, 0.06%, 0.07%, 0.08%, 0.09%, 0.1%, 0.11%, or 0.12% w/v.

Figure 9:
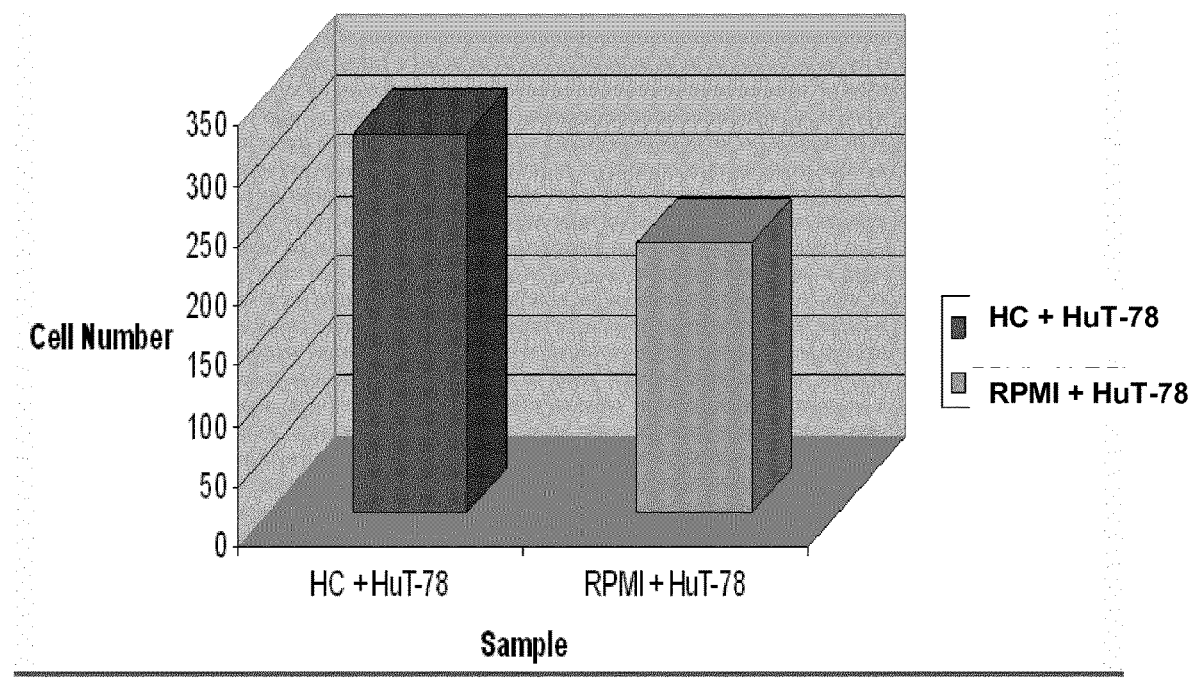
FIG. 9 depicts cell numbers in suspension cultures of Hut 78 cells after 3 days incubation in RPMI media in the presence of and in the absence of the cell culture medium additive (designated "HC" in the figure).

Example 10—Cell Proliferation and Cell Viability Characteristics of Cultures Grown in Cell Culture Media Containing the Additive The cell count of Hut 78 cells in suspension culture samples was measured after 3 days incubation in media with (designated "HC") and without the cell culture media additive. Cells seeded at a density of 5×104/ml were incubated in RPMI culture with (designated "HC") and without the cell culture media additive of the formulation previously described (0.06 v/w) for 3 Days (72 hours) in 96 well micro titre plate. Prior to sampling cell suspensions were thoroughly mixed and small aliquots of cell suspension were removed and cell number assessed by digital microscopy and image analysis. The results—as depicted in FIG. 9—illustrate that cells appear to proliferate more quickly when held in suspension as facilitated by the cell culture media additive.

Figure 11:
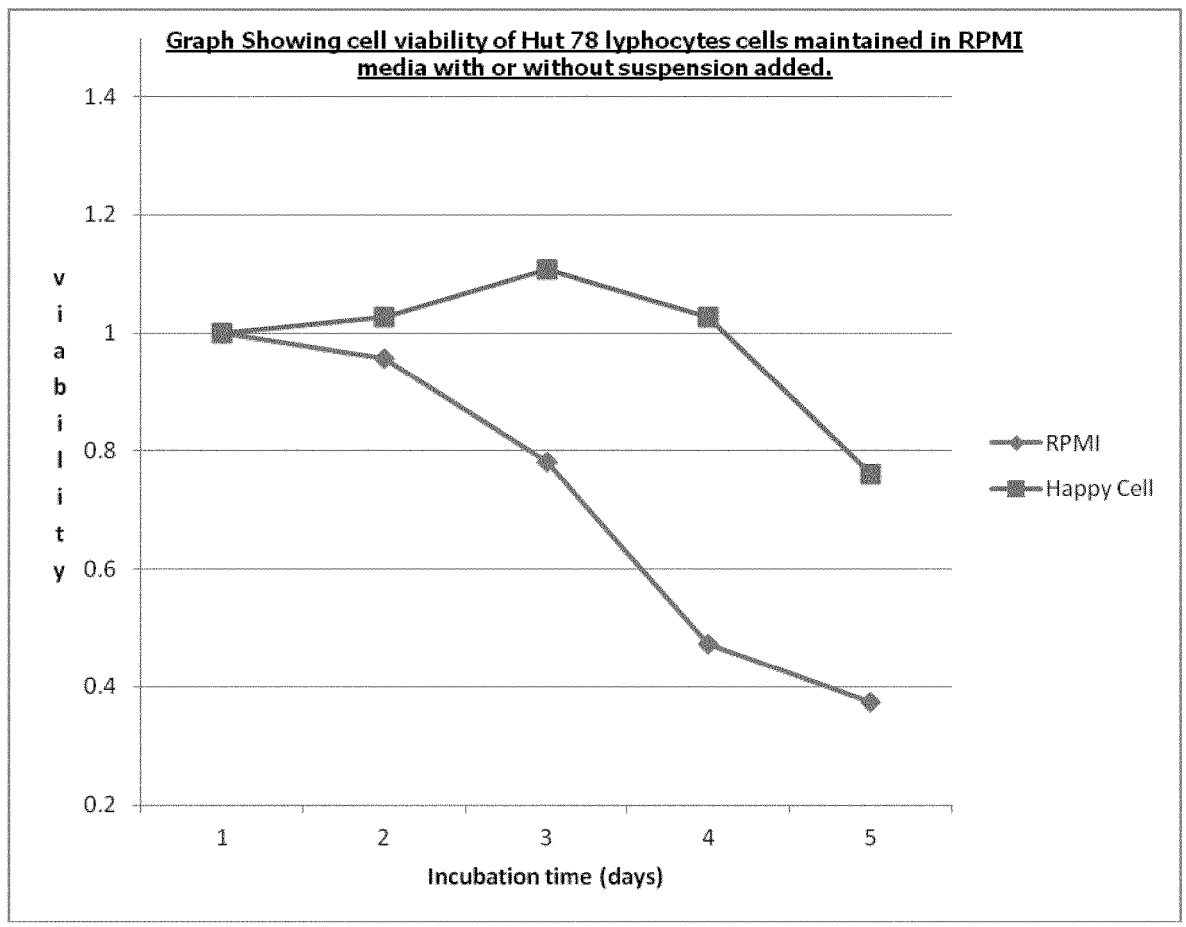
FIG. 11 depicts preliminary results of an assessment of cell viability (as assessed by flow cytometry) of cells maintained in RPMI either in the presence or absence of the cell culture additive (designated "Happy Cell" in the figure).

A preliminary assessment of the viability of cells grown in the presence of the cell culture media additive was performed by investigation using flow cytometry. Hut 78 cells were maintained in RPMI culture media in the presence/absence of the additive of the formulation previously described (0.06% w/v) at 37 degrees Celsius and 5% CO2 for periods ranging from 1 to 5 days. Viability was assessed using a Beckman Coulter CyAn Color flow cytometer by measuring forward scatter vs side scatter profiles. This was used to exclude debris but to include live and dead cells; wherein live and dead cells were then analyzed on Forward Scatter vs Propidium Iodide (final concentration 1 ug/mL). The percentage of live cells per sample was then noted. These preliminary results are depicted in FIG. 11 (additive-containing medium is designated "Happy Cell"), wherein the data is represented as cell viability values normalized to day 1 of the experiment to compensate for any small variances in initial seeding density.

It has also been noted on many occasions that cells such as t lymphocytes tend to grow more rapidly when maintained in media containing the additive than in media without the additive although it should be noted that these early observations need to be qualified and cross validated using a range of assay approaches.

Example 11—Flow Cytometry

A key application area that has been identified for the cell culture media additive is flow cytometry. In automated flow cytometry, samples are loaded into high-density microplates (96, 384 and 1536 wells) and may not be analyzed for many hours. One major problem associated with this is the tendency of cells to sediment quickly to the bottom of the wells of these plates resulting in cell clumping (which may clog the cytometer fluidic delivery systems) and also once sedimentation of cells has occurred, it is less likely for them to be picked up by the sample collector and hence will remain at the bottom of the well plate unanalyzed.

Figure 12:
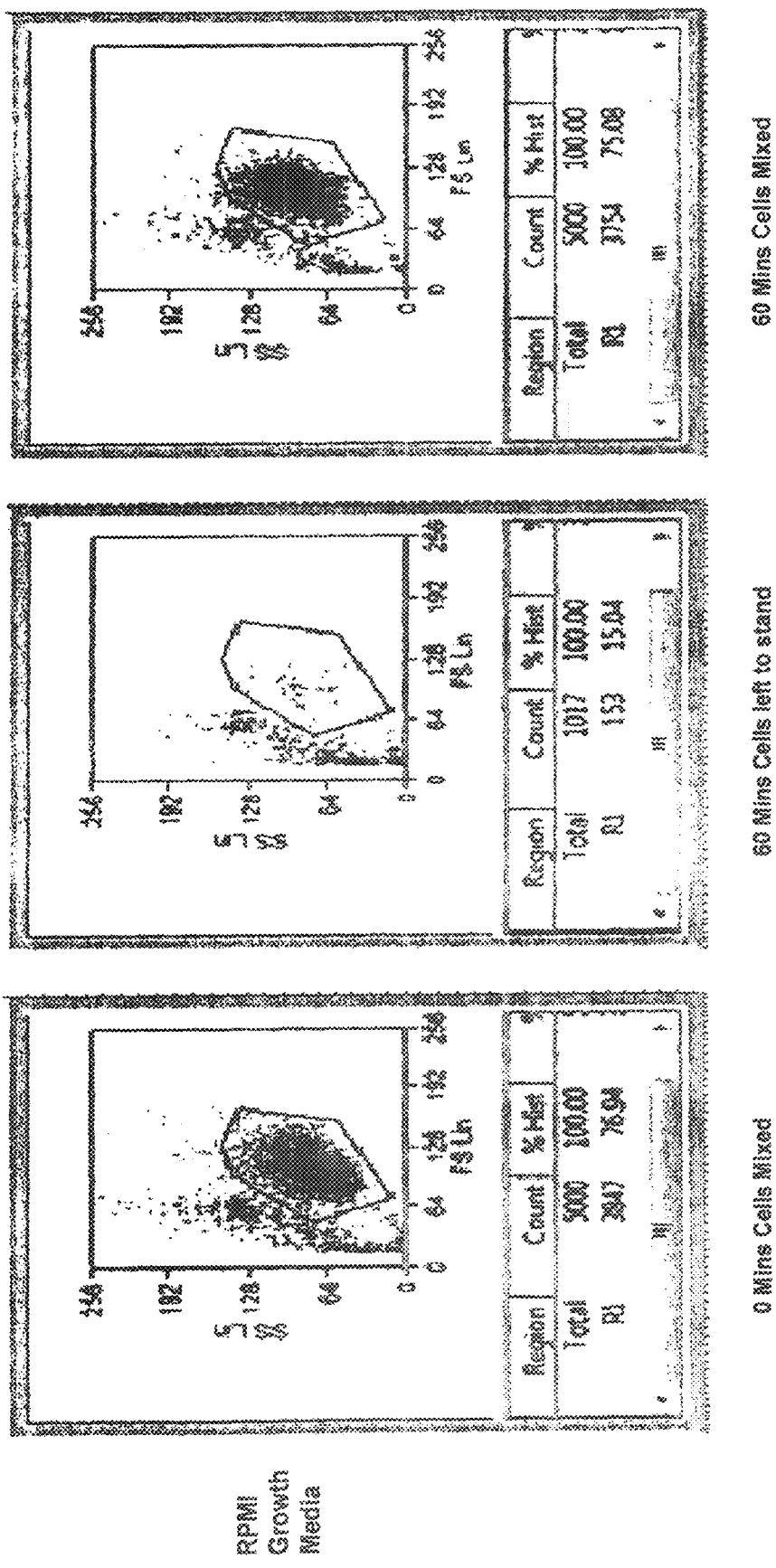
FIGS. 12 and 13 depict a dot plot of samples taken by flow cytometry of cell suspensions in the presence and absence of the cell culture additive (designated "HC" in the figures) over a number of stages.
Figure 13:
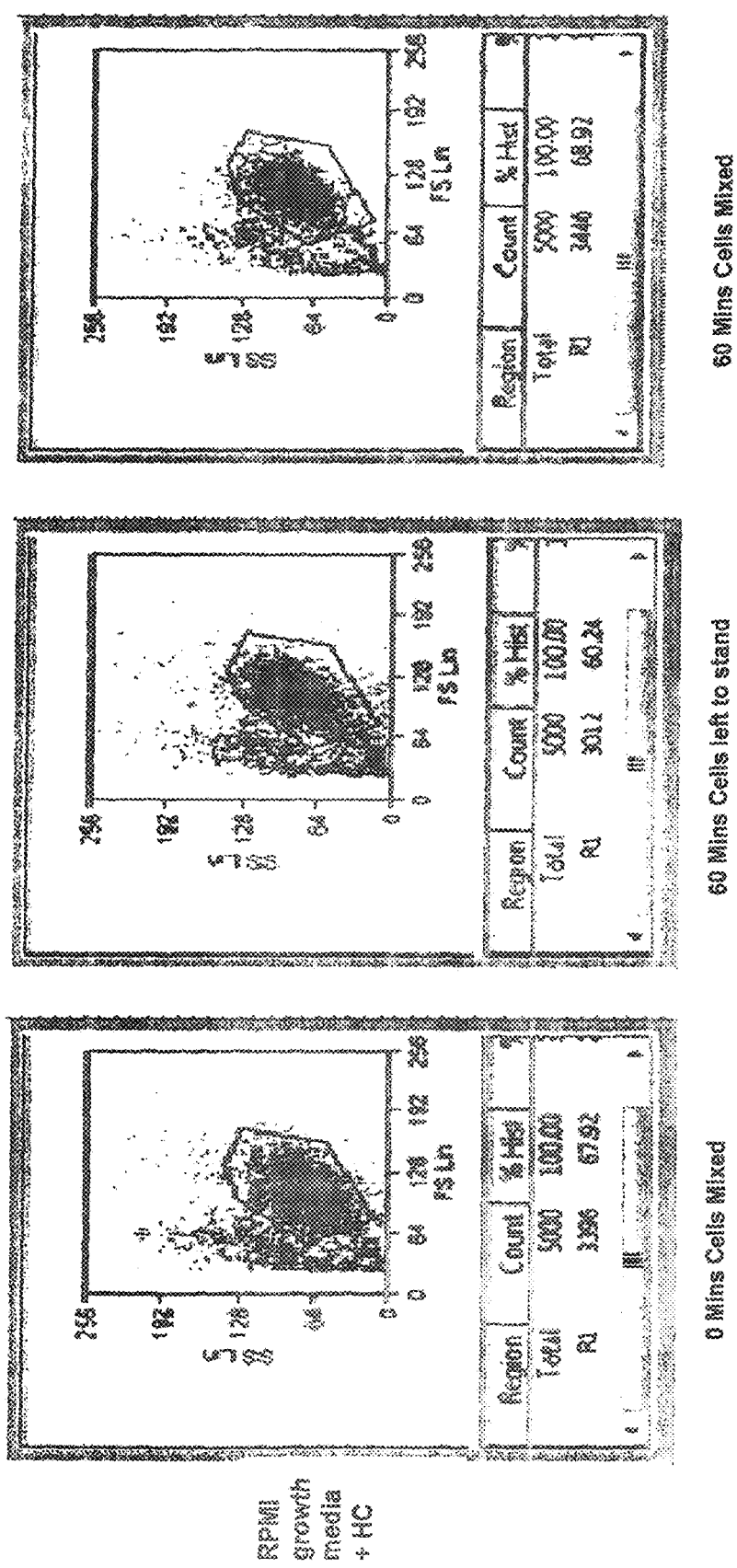
Figure 14:
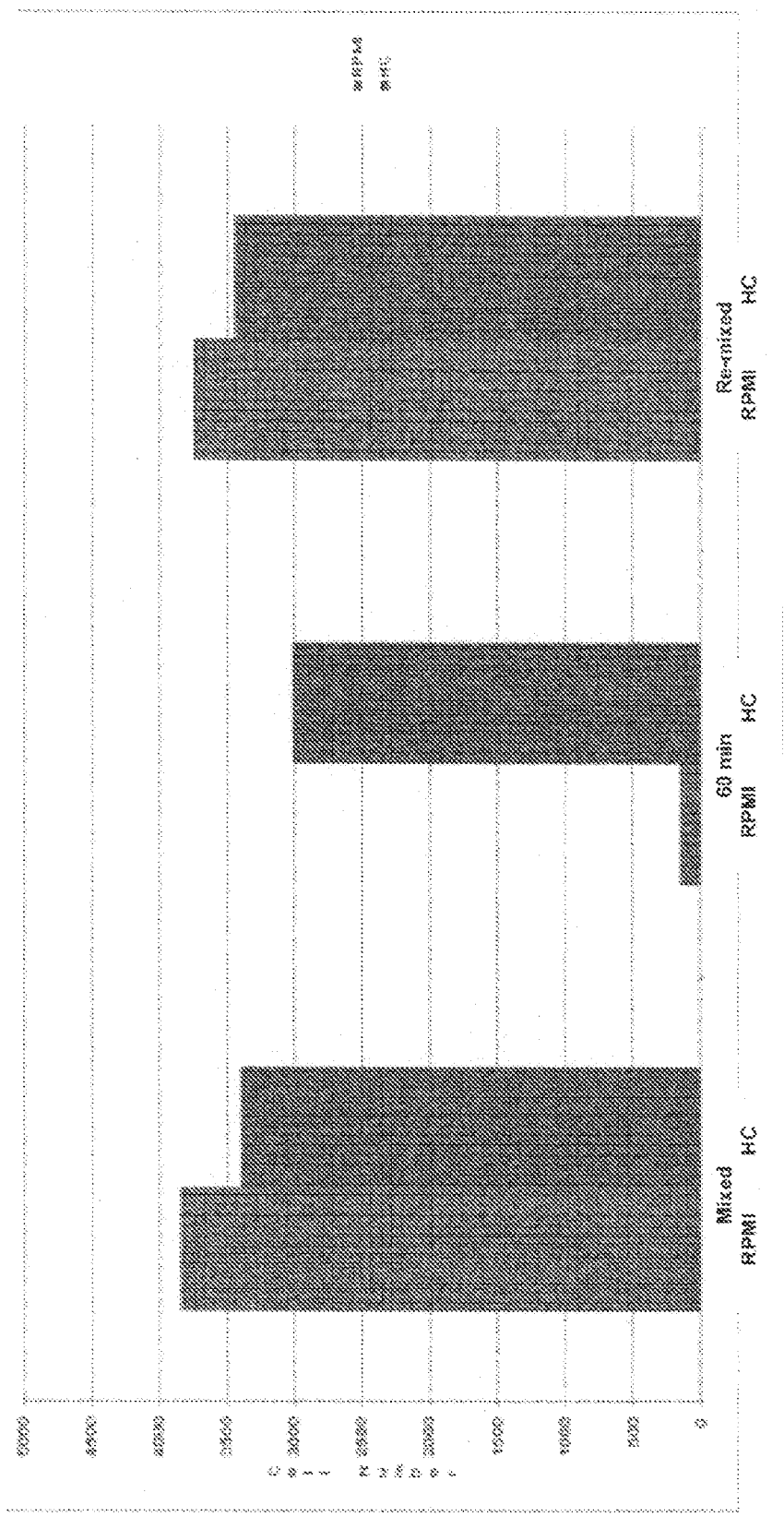
FIG. 14 is a cell count graph derived from the dot plot data of FIGS. 12 and 13.

FIGS. 12-14 present experimental results that demonstrate the utility of the additive with respect to flow cytometry. Cell suspensions of Hut 78 cells in growth media comprising RPMI with or without the additive (designated HC in the figures) of the formulation previously described at 0.06 w/v % were mixed and then sampled using a flow cytometer. Foetal Calf Serum was not used in this experiment. 10% Cell suspensions were then left to stand for 60 mins, sampled again and then finally remixed and sampled. As can be seen from the dot plot (raw data, FIGS. 12 and 13) and the cell count graph below (FIG. 14), the RPMI+ additive suspension shows small changes in the number of cells collected by the cytometer between zero and 60 minutes, whereas the RPMI-only suspension cell count is dramatically reduced at the same time point. The analysis of these cells is only possible once re-mixing has taken place (and the cells have thus been temporarily re-suspended). Cell number was assessed using a Beckman Coulter CyAn Color flow cytometer by measuring forward scatter vs side scatter profiles. This was used to exclude debris but to include live and dead cells.

Example 12—Sedimentation of Cells from Suspension

It was decided also to investigate the feasibility of employing enzymatic digestion of the additive using an appropriate polysaccharide-digesting enzyme (in this case the commercially available "Biocellulase A Conc" as supplied by the Kerry Ingredients and Flavours Ltd) to precipitate the cells. Biocellulase A Conc is an enzymatic preparation that can be used to digest a wide range of polysaccharides. It is known to exhibit a level of beta-mannanase activity, and as such was a possible candidate for digesting the mannan polysaccharide constituent of the additive. It will hereafter be referred to as "Biocellulase A".

It has been demonstrated the cell culture medium additive is capable of maintaining cells in suspension for many weeks. Although desirable for culture of multi-cellular structures or expanding cellular populations by means of cell proliferation, medium containing the additive like many other commonly used 3D scaffold technologies such as agar and protein based hydro gels do not allow for the convenient analysis by means of standard laboratory techniques (such as proteomics, genomics, microscopy, imuno histochemistry). In almost every case, the biggest barrier to these analysis methods is gaining access to the cellular material by liberating from the scaffold material. The use of enzymatic digestion of the constituent polymers of the additive to liberate cellular material to enable easy sample preparation and analysis was therefore investigated.

Figure 15:
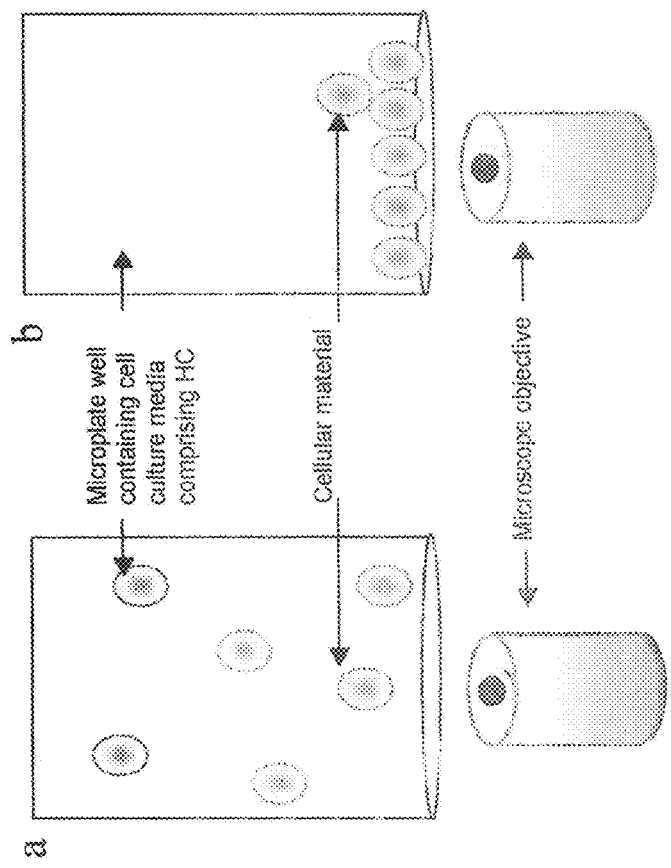
FIG. 15 is a schematic of experimental set up used to determine the efficacy of Biocellulase A digestion on the sedimentation of single cells and multi-cellular structures suspended in media containing the cell culture medium additive (designated "HC" in the figure), as utilized for example, to produce the images in FIGS. 6a and 6b.

The aim of the study was to first determine (a) whether the use of Biocellulase A would permit the imaging, extraction and manipulation of single cells and multi cellular aggregates and (b) whether this enzyme had any effect on cell viability. The method for determining the efficacy of this approach is shown in the schematic of FIG. 15.

Figure 6A:
FIGS. 6a and 6b depicts images of the well bottom of a micro-plate containing A549 cells in RPMI media containing the cell culture medium additive before (6a) and 120 minutes after (6b) treatment with Biocellulase A.
Figure 6B:
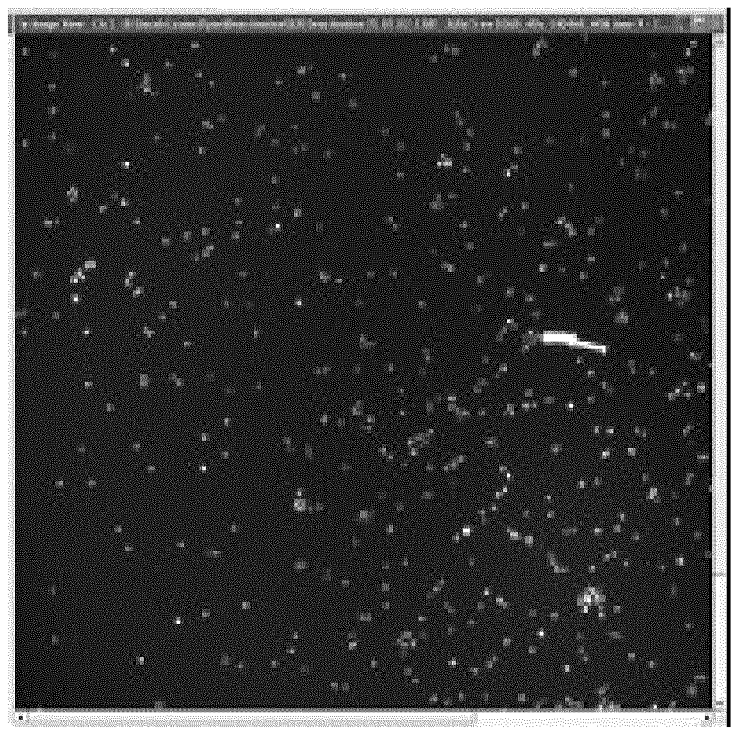

FIGS. 6a and 6b are images of the well bottom of micro-plate containing A549 cells in RPMI media containing the additive before (FIG. 6a) and 120 minutes after (FIG. 6b) treatment with Biocellulase A. 100 μl of fluorescently labelled A549 lung cancer cells in RPMI growth media with and without the additive of the formulation previously described above (and at 0.06% w/v) were added to a 96-well low attachment plate and incubated at 37 degrees Celsius for 30 minutes. Following incubation, 20 μl of Biocellulase A (deactivation agent) at a concentration of 300 mg/L was added to each of the wells. Sedimentation was then assessed by means of digital microscopy. As can be seen, a greater number of cells are visible after enzymatic treatment.

Figure 8:
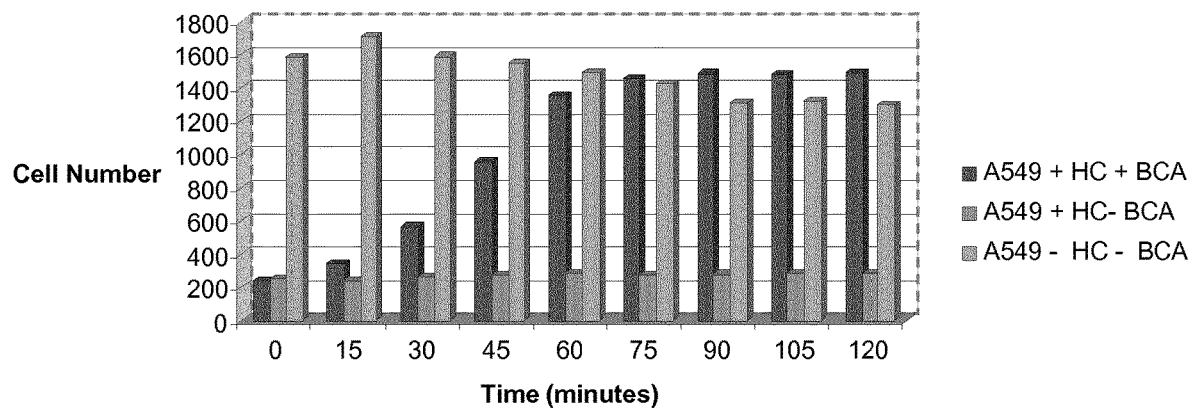
FIG. 8 depicts the effects of Biocellulase A (BCA) on sedimentation of cells grown in RPMI media in the presence of the cell culture medium additive (designated "HC in the figure).

FIG. 8 shows the effects of Biocellulase A digestion of the polysaccharide components of the additive. 100 μl of fluorescently labelled A549 lung cancer cells in RPMI growth media with and without the additive of the formulation previously described above (0.06% w/v) were added to a 96-well low attachment plate and incubated at 37 degrees Celsius for 30 minutes. Following incubation, 20 μl of Biocellulase A (deactivation agent) at a concentration of 300 mg/L was added to each of the wells. Sedimentation was then assessed by means of digital microscopy and image analysis at times ranging from 0 to 120 minutes. Data shown represents number of cells recorded at the bottom of the micro-plate well (per the schematic of FIG. 15) when incubated in the following conditions (i) A549, with medium containing additive ("HC"), and also with Biocellulase A (BCA) (ii) A549 with medium containing additive ("HC"), and without Biocellulase A (BCA) c) A549 with medium without additive (RPMI) and without Biocellulase A (BCA). As can be seen, while little sedimentation of cells takes place when suspended in media containing the additive, these cells may precipitate out upon addition of BCA.

Figure 7:
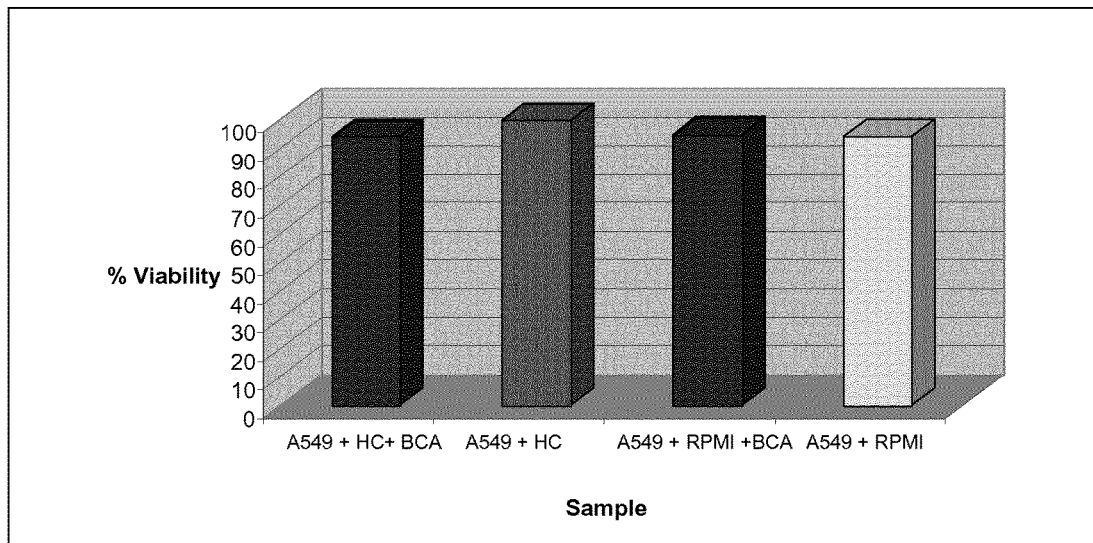
FIG. 7 depicts the results of an investigation into the effect of Biocellulase A (BCA) on A549 Lung Cancer cell viability in RPMI media both in the presence of and in the absence of the cell culture medium additive (designated "HC" in the figure).

FIG. 7 showing the effects of the enzyme Biocellulase A on the viability of A549 Lung cancer cells grown in RPMI with and without the additive. 100 μl of fluorescently labelled A549 lung cancer cells in RPMI growth media with and without the additive of the formulation previously described above (0.06% w/v) were added to a 96-well low attachment plate containing 20 μl of Biocellulase A (deactivation agent at a concentration of 300 mg/L). Following a 120 minute incubation at 37 Degrees Celsius and 5% CO2 the dead cell dye Propidium Iodide then added to each well at final concentration of 1 ug/mL1 and cell viability was assessed by means of digital microscopy and image analysis. Data shown represents percentage of viable cells (Propidium Iodide negative) present in each well. Dead cells were stained Propidium Iodide positive. Cells were incubated in the following conditions:

(i) A549 with medium containing additive ("HC") and with Biocellulase A (BCA)

(ii) A549 with medium containing additive ("HC"), and without Biocellulase A (BCA)
(iii) A549 with medium without additive (RPMI) and with Biocellulase A (BCA)
(iv) A549 with medium without additive (RPMI) and without Biocellulase A (BCA)

As can be seen, there is little difference in the cell viability levels, implying that the enzyme-based sedimentation technique has no effect on cell viability.

Furthermore an investigation was conducted into the effects of the biocellulase A digestion of the additive both on the precipitation of single cells in suspension and multicellular bodies which have been formed from a variety of cell types including CHO-k1, A549 and prostate tumor cells (results not shown). Further to this Biocellulase A was tested at final concentrations up to 100 mg/L for periods of time ranging from 120 minutes (FIG. 7) to 72 hours and did not show any discernible reduction in the viability of Hut 78 cells maintained in the presence of this enzyme.

While these experiments have been performed using Biocellulase A, which has beta-mannanase activity, it will be appreciated that the enzymatic sedimentation/precipitation method may be performed using other suitable enzymes. A wide range of enzymes have some beta-mannanase activity, and while this may not be their primary activity, they may nevertheless be suitable potential candidate enzymes. Additional enzyme preparations may comprise but are not limited to those with beta-d-mannanase, a-amylase, glucosidase, α-d-mannosidase, β-d-glucanase, xanthan lyase or alpha-galactosidase activities as appropriate, depending on the polysaccharide constituents in the additive. Such enzyme preparations may be used alone or in conjunction with one another or with an enzyme preparation having beta-mannanase activity such as Biocellulase A. Alternate combinations may be used to reduce the chances of experimental error due to their inhibition by assay components such as test compounds.

Finally, it was considered necessary to investigate the possibility that the polysaccharide digestion could result in unwanted byproducts (in particular, glucose) that could adversely influence cell behaviour. Glucose production would be a highly undesirable external stimulus that could hinder the study of cell behaviour/cell characteristics of cells cultured or suspended in additive-containing media.

A comparative test was carried out on additive-containing media with and without the deactivation agent Biocellulase A. The objective of this test was to determine that Biocellulase A does not cause an increase in the glucose concentration of the additive-containing media. This test was carried out using glucose test strips (Merckoquant Cat. #1.17866.0001), which use a colour gradient as a means by which to indicate the glucose level of the substance in question.

An equivalent volume of Biocellulase A was added to 3 equal volumes of additive-containing media (additive of formulation previously described) at 2 concentrations, 0.12 w/v and 0.06 w/v, in a 96 well plate. Samples additive-containing media on its own (i.e. without Biocellulase A), 0.12 w/v and 0.06 w/v, was setup as a control. This plate was then incubated at 37° C. and 5% CO2. At time-points of 30, 45 and 60 minutes after incubation, a sample of 0.12 w/v and 0.06 w/v additive-containing media plus Biocellulase A was tested with a glucose strip. These time intervals are comparative with the time taken for the deactivation agent to work, and the test was carried out under experimental conditions. After testing the strips were allowed to stand for 1 minute, in accordance with the manufacturers instructions.

The colour of the strip was then compared to the colour chart provided with the glucose test. The test strips were also compared to various concentration controls that were put in place.

The glucose strips, for every time point and each concentration, exhibited the same colour, indicating a glucose level in the range of 50-100 mg/l. When compared to the control of additive containing media alone a similar colour was observed, indicating a similar level of glucose in the additive containing media alone as when combined with the Biocellulase A. The test strips were also compared to the concentration controls and were found to fit in the 50-250 mg/l range, verifying the above observation. Therefore, it can be concluded that the addition of Biocellulase A does not increase the glucose concentration of the additive containing media over time.

Where the terms xanthan, galactomannan, glucomannan, mannan, Guar, Cassia, Fenugreek, Tara, locust bean gum, *konjac*, Guar gum, Cassia gum, Fenugreek gum, and Tara gum have been used without any further qualification, these definitions relate to polysaccharides in either their native form or in modified forms thereof.

As has previously been stated, the cell culture medium may comprise any conventional medium suitable for growing or suspending cells. Accordingly, the term "cell suspension medium" may be taken to mean any medium in which it is possible to suspend cells. Insofar as the term "cell culture medium additive" is used above, it will be readily understood to mean an additive that may be added to a given medium in order to improve the capacity of the medium to suspend cells and multi-cellular bodies. It will be readily appreciated that an additive described in such a way is not solely intended for nor limited to use in conjunction with cell media where the prime purpose is to culture cells, and that the additive may equally be used in conjunction with any media where the primary goal is to suspend rather than to culture the cells per se.

It will be appreciated that—inkeeping with standard tissue culture practice—all media experiments performed with cells as described above were performed in the presence of 10% Foetal Calf Serum unless expressly stated otherwise.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any suitable sub-combination.

The invention claimed is:

1. A composition comprising a liquid cell growth medium and cells suspended therein, wherein said liquid cell growth medium comprises:
    a liquid cell culture medium and an amount of between 0.01% and 0.36% w/v of xanthan and galactomannan polysaccharides having a ratio of xanthan polysaccharide to galactomannan polysaccharide of between 60:40 and 20:80 w/w, wherein:
    said liquid cell growth medium is non-toxic to said cells;
    said liquid cell growth medium has a viscosity sufficient to prevent said cells from falling out of suspension while also allowing said liquid cell growth medium to be dispensed using a liquid dispensing device; and said cells are not microbial cells.

2. The composition of claim 1, wherein the galactomannan polysaccharide has a galactose content of at least 16% by weight.

3. The composition of claim 1, wherein the galactomannan polysaccharide is at least one type of gum selected from the group consisting of guar gum, locust bean gum, tara gum, cassia gum and fenugreek gum.

4. The composition of claim 1, wherein the galactomannan polysaccharide has been enzymatically modified to reduce the galactose content.

5. The composition of claim 4, wherein the galactomannan polysaccharide has been enzymatically modified using α-galactosidase.

6. The composition of claim 1, wherein the xanthan and galactomannan polysaccharides are present in the liquid cell growth medium in a final concentration that is about 0.018% w/v.

7. The composition of claim 1, wherein the xanthan and galactomannan polysaccharides are present in the liquid cell growth medium in a final concentration that is about 0.06% w/v.

8. The composition of claim 1, wherein the xanthan and galactomannan polysaccharides are present in the liquid cell growth medium in a final concentration that is about 0.24% w/v.

9. The composition of claim 1, wherein said liquid cell culture medium is selected from the group consisting of Dulbecco's modified Eagle's medium (DMEM), Roswell Park Memorial Institute (RPMI) medium and Eagle's minimal essential medium (EMEM).

10. The composition of claim 1, wherein said cells are in the form of multi-cellular bodies.

11. The composition of claim 1, wherein said cells are selected from the group consisting of animal cells, plant cells, human cells, hamster cells, cancer cells, stem cells, tumor cells, Chinese Hamster Ovary cells, lymphocytes, multi-cellular bodies, spheroids, and embryoid bodies.

12. A method of preparing the composition of claim 1 comprising the step of adding to a liquid cell culture medium an amount of between 0.01% and 0.36% w/v of xanthan and galactomannan polysaccharides having a ratio of xanthan polysaccharide to galactomannan polysaccharide of between 60:40 and 20:80 w/w, and cells, wherein:

said liquid cell growth medium is non-toxic to said cells;

said liquid cell growth medium has a viscosity sufficient to prevent said cells from falling out of suspension while also allowing said liquid cell growth medium to be dispensed using a liquid dispensing device; and said cells are not microbial cells.

13. The method of claim 12, wherein the galactomannan polysaccharide has a galactose content of at least 16% by weight.

14. The method of claim 12, wherein the galactomannan polysaccharide is at least one type of gum selected from the group consisting of guar gum, locust bean gum, tara gum, cassia gum and fenugreek gum.

15. The method of claim 12, wherein the galactomannan polysaccharide has been enzymatically modified to reduce the galactose content.

16. The method of claim 15, wherein the galactomannan polysaccharide has been enzymatically modified using α-galactosidase.

17. The method of claim 12, wherein the xanthan and galactomannan polysaccharides are present in said liquid cell growth medium in a final concentration that is about 0.018% w/v.

18. The method of claim 12, wherein said cells are selected from the group consisting of animal cells, plant cells, human cells, hamster cells, cancer cells, stem cells, tumor cells, Chinese Hamster Ovary cells, lymphocytes, multi-cellular bodies, spheroids, and embryoid bodies.

19. A method of sedimenting cells comprising:

(i) providing a liquid cell growth medium and cells suspended therein, wherein said liquid cell growth medium comprises:

a liquid cell culture medium and an amount of between 0.01% and 0.36% w/v of xanthan and galactomannan polysaccharides having a ratio of xanthan polysaccharide to galactomannan polysaccharide of between 60:40 and 20:80 w/w, wherein:

said liquid cell growth medium is non-toxic to said cells;

said liquid cell growth medium has a viscosity sufficient to prevent said cells from falling out of suspension while also allowing said liquid cell growth medium to be dispensed using a liquid dispensing device; and said cells are not microbial cells; and (ii) adding a polysaccharide-digesting enzyme to said liquid cell growth medium, wherein said enzyme is capable of digesting the xanthan and galactomannan polysaccharides, thereby reducing the capacity of said liquid cell growth medium to suspend said cells such that said cells can sediment out of suspension.

* * * * *